(12) United States Patent
Bonny et al.

(10) Patent No.: US 10,806,517 B2
(45) Date of Patent: Oct. 20, 2020

(54) IMPLANT BASED PLANNING, DIGITIZING, AND REGISTRATION FOR TOTAL JOINT ARTHROPLASTY

(71) Applicant: THINK SURGICAL, INC., Fremont, CA (US)

(72) Inventors: Daniel Patrick Bonny, Fremont, CA (US); Joel Zuhars, Fremont, CA (US); Michael E. Hoppe, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 128 days.

(21) Appl. No.: 16/215,055

(22) Filed: Dec. 10, 2018

(65) Prior Publication Data

US 2019/0105108 A1    Apr. 11, 2019

Related U.S. Application Data

(63) Continuation of application No. 15/532,284, filed as application No. PCT/US2015/064258 on Dec. 7, 2015, now Pat. No. 10,194,991.

(Continued)

(51) Int. Cl.
*A61B 34/10* (2016.01)
*A61B 34/20* (2016.01)
(Continued)

(52) U.S. Cl.
CPC ............ *A61B 34/10* (2016.02); *A61B 17/154* (2013.01); *A61B 17/1675* (2013.01);
(Continued)

(58) Field of Classification Search
CPC .................................................... A61B 34/10
See application file for complete search history.

(56) References Cited

U.S. PATENT DOCUMENTS 5,086,401 A    2/1992  Glassman et al.
5,198,877 A *  3/1993  Schulz .................. G01S 7/4813
                                                       356/614

(Continued)

FOREIGN PATENT DOCUMENTS

WO       9107726 A1    5/1991
WO    2014145591 A2    9/2014
WO    2014150428 A2    9/2014

OTHER PUBLICATIONS

International Search Report dated Apr. 8, 2016 for International Application No. PCT/US2015/064258 filed Dec. 7, 2015.

(Continued)

*Primary Examiner* — Christian A Sevilla
(74) *Attorney, Agent, or Firm* — Blue Filament Law PLLC

(57) ABSTRACT

A system and process for performing orthopedic surgery is provided that uses a patient's existing implant as a registration tool in an orthopedic surgical procedure. The systems and processes may be used with computer assisted systems or navigation systems to aid in the removal of bone, bone cement, or a bone prosthesis, typically a bone prosthesis used in hip replacement surgery, knee replacement surgery, and the like. The removal of the prosthesis may be done by conventional methods, with navigation systems, robotic assistance or articulating hand held systems. The removal of bone and/or bone cement may be performed with navigated systems, robotic systems, articulating hand-held systems and combinations thereof.

14 Claims, 3 Drawing Sheets

Related U.S. Application Data

(60) Provisional application No. 62/088,896, filed on Dec. 8, 2014.

(51) Int. Cl.

| | | |
|---|---|---|
| *A61B 34/30* | (2016.01) | |
| *A61B 17/15* | (2006.01) | |
| *A61B 17/16* | (2006.01) | |
| *A61B 17/17* | (2006.01) | |
| *A61F 2/38* | (2006.01) | |
| *A61F 2/30* | (2006.01) | |
| *A61F 2/46* | (2006.01) | |

(52) U.S. Cl.
CPC ...... *A61B 17/1703* (2013.01); *A61B 17/1764* (2013.01); *A61B 34/20* (2016.02); *A61B 34/30* (2016.02); *A61F 2/389* (2013.01); *A61B 17/15* (2013.01); *A61B 2034/102* (2016.02); *A61F 2002/3069* (2013.01); *A61F 2002/4632* (2013.01); *A61F 2002/4633* (2013.01)

(56) References Cited

U.S. PATENT DOCUMENTS

| | | | |
|---|---|---|---|
| 5,383,454 A | 1/1995 | Bucholz | |
| 5,769,092 A * | 6/1998 | Williamson, Jr. | .. A61F 2/30942 128/898 |
| 6,033,415 A | 3/2000 | Mittelstadt et al. | |
| 7,497,828 B1 * | 3/2009 | Wilk | ..... A61B 8/4494 600/443 |
| 7,981,158 B2 * | 7/2011 | Fitz | ..... A61B 5/4528 623/17.16 |
| 8,165,366 B2 * | 4/2012 | Haimerl | ..... A61B 90/36 382/128 |
| 8,801,720 B2 | 8/2014 | Park et al. | |
| 9,101,394 B2 * | 8/2015 | Arata | ..... G06F 19/00 |
| 2011/0107270 A1 | 5/2011 | Wang et al. | |
| 2014/0025348 A1 | 1/2014 | Abiven | |
| 2014/0208578 A1 | 7/2014 | Linderman et al. | |
| 2017/0258532 A1 | 9/2017 | Shalayev et al. | |

OTHER PUBLICATIONS

Supplementary European Search Report dated May 23, 2018 for European Application No. 15868129 filed Dec. 7, 2015.

* cited by examiner

IMPLANT BASED PLANNING, DIGITIZING, AND REGISTRATION FOR TOTAL JOINT ARTHROPLASTY

CROSS REFERENCE TO RELATED APPLICATIONS

This application is a continuation of U.S. Nonprovisional application Ser. No. 15/532,284 filed 1 Jun. 2017; that in turn is a US national phase filing of PCT/US2015/064258, filed 7 Dec. 2017; and in turn claims priority benefit of U.S. Provisional Application Ser. No. 62/088,896 filed 8 Dec. 2014; the contents of which are hereby incorporated by reference.

FIELD OF THE INVENTION

The present invention relates generally to the field of computer-aided surgical systems, and more specifically to a new and useful method for performing computer-aided total joint arthroplasty.

BACKGROUND OF THE INVENTION

Total joint replacement (TJR) (also called primary total joint arthroplasty) is a surgical procedure in which the articulating surfaces of a joint are replaced with prosthetic components, or implants. TJR has proven to be a successful procedure, especially for hips, knees, shoulders, and ankles, and allows people to restore functionality while greatly reducing pain associated with osteoarthritis.

Bone is a living tissue that is constantly changing through the resorption of matrix by osteoclasts and the deposition of new matrix by osteoblasts. Articular cartilage is an avascular tissue that is found on the surfaces of joints and serves to provide a smooth interface upon which bones can articulate with each other. TJR an orthopedic procedure in which the typically-worn articular surfaces of the joint are replaced with prosthetic components, or implants. TJR typically requires the removal of the articular cartilage of the joint including a varying amount of bone depending on the joint and the implant being used. This cartilage and bone is then replaced with synthetic implants, typically metal or plastic, that are used to create new joint surfaces.

The replacement implants used in joint replacement surgeries have a limited life expectancy and will sometimes need to be replaced. Replacement of a TJR implants is called revision total joint replacement (RTJR) and involves removing the old implant(s) from the bone, removing any bone cement (poly(methyl methacrylate) or PMMA) used during the TJR, reshaping the bone to fit new revision implant(s), and placing the new revision implant(s) into the bone. RTJR is known to be a difficult and lengthy procedure because the surgeon typically has a limited amount of information about the location and amount of bone cement from the previous TJR. Removal of both the old implant and the bone cement is typically performed using a variety of hand tools including osteotomes, saws, punches, power saws, power burs, and ultrasonic instruments. However, these tools can be tedious to use, especially when trying to remove bone cement from deeper cavities or small holes. Additionally, these tools present a risk of fracturing the bone when removing the implant or the bone cement. To increase visibility of the bone cement and bone-implant interface, holes or windows may be cut or drilled into the bone; however, these procedures have the propensity to weaken the bone and increase the risk of later fracture.

Revision joint arthroplasty is a technically difficult procedure that often presents intraoperative challenges. For example, difficulties in removing the previous implant or the bone cement may result in an excess removal of healthy bone. Additionally, the bone structure may be damaged from the tools and the length of time required to adequately remove all of the bone cement, may put the patient's safety at risk. A computer implemented system and method for removing bone cement or other material is described in U.S. Pat. No. 5,769,092 assigned to the assignee of the present application. However, there have been advances in imaging which may allow for an improved removal of bone and or bone cement during a revision joint arthroplasty. Thus, there exists a need for a more effective process to adequately remove the previous implant, any bone cement, and prepare a new cavity for a revision implant without further compromising the structure of the bone.

SUMMARY OF THE INVENTION

A method for revision of a total knee replacement (TKR) for a patient includes the performance of an imaging scan of a bone with an installed implant. The installed implant and the bone outside the implant region are segmented. A three dimensional (3D) model based on the manufacturers specifications of the installed implant is then obtained. The manufacturer's 3D model to the segmented implant is registered to generate a transformation matrix thereof. The transformation matrix is applied to a set of digital imaging and communications in medicine (DICOM) data of the patient. The TKR is revised with a new implant for the patient based on a pre-operative plan so produced.

A surgical system is also provided that includes an input device capable of receiving data from an image of a bone with an installed prosthesis. A database contains three dimensional (3D) models and manufacturing specifications of the installed prosthesis. A computer processor unit (CPU) is provides that segments the installed prosthesis and the bone outside the prosthesis region, registers the manufacturer's 3D model to the segmented implant and generates a transformation matrix thereof. A surgical tool is provided that computes the transformation matrix from the implant to a set of digital imaging and communications in medicine (DICOM) data of the patient to perform a surgical procedure.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DESCRIPTION OF THE INVENTION

Figure 1:
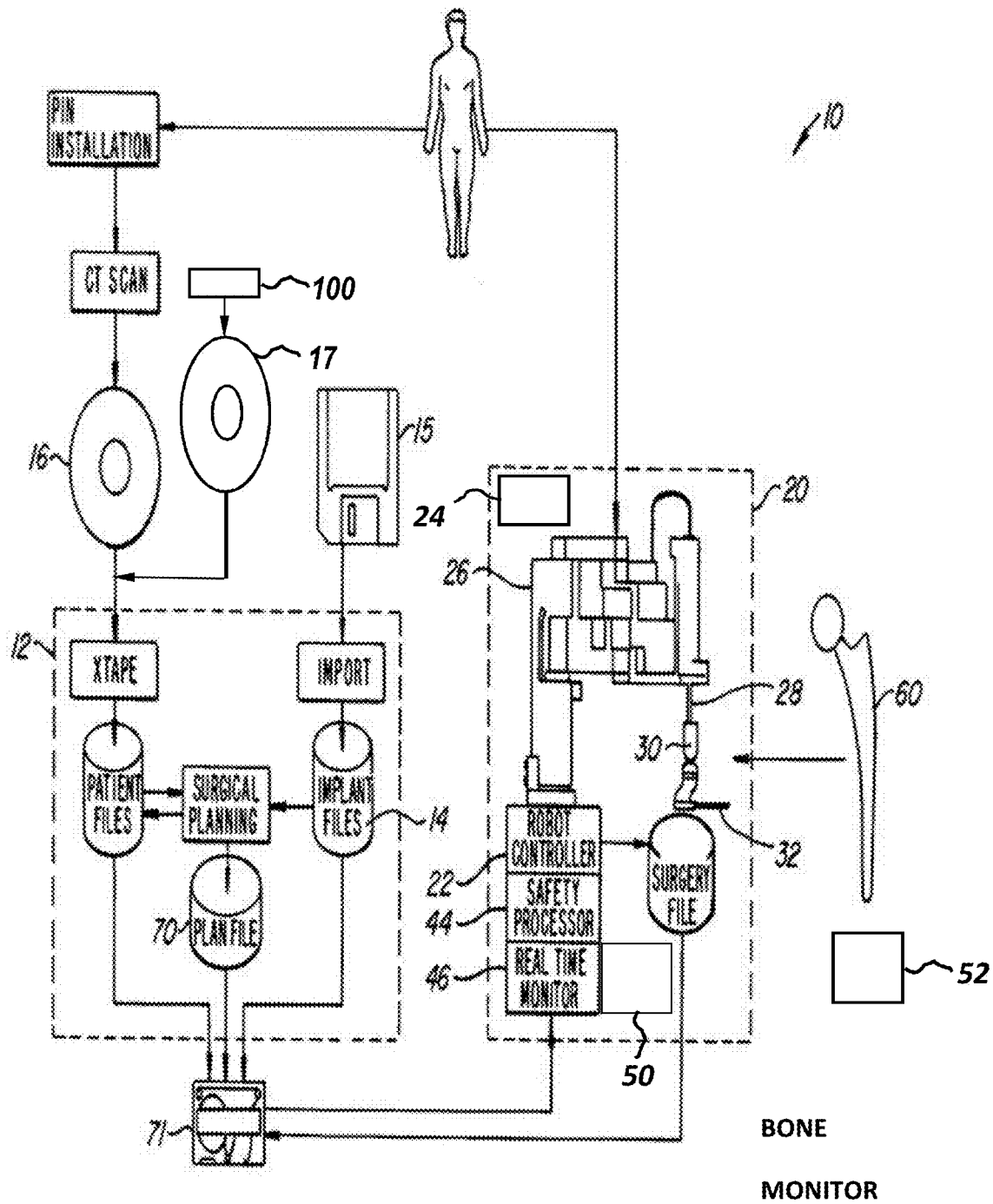
FIG. 1 illustrates the architecture of a surgical robotic system for performing an implant revision according to the present invention.

The present invention has utility as a system and process for performing orthopedic surgery. The following description of various embodiments of the invention is not intended to limit the invention to these specific embodiments, but rather to enable any person skilled in the art to make and use this invention through exemplary aspects thereof. Disclosed herein are systems and processes to use a patient's existing implant as a registration tool in orthopedic surgery. Further, the systems and processes may be used with computer assisted systems or navigation systems to aid in the removal of bone, bone cement, or a bone prosthesis, typically a bone prosthesis used in hip replacement surgery, knee replacement surgery, and the like. The removal of the prosthesis may be done by conventional methods, with navigation systems, robotic assistance, or articulating hand held systems. The removal of bone and/or bone cement, may be performed with navigated systems, robotic systems, articulating hand-held systems, and combinations thereof. Examples of robotic systems, navigation systems, and articulating hand-held system that may be used with the disclosed invention may include the ROBODOC Surgical System (THINK Surgical, Inc.), NavioPFS System (Blue Belt Technologies, Inc.), RIO Robotic System (Mako Surgical Corp.), OrthoMap ASM knee navigation (Stryker Corporation), a navigated freehand saw (TRAK Surgical), navigated cutting guides, 4 degree of freedom saw, a system with one to seven degrees of freedom, an articulating hand-held system with at least one degree of freedom, an articulating hand-held drilling system as disclosed by the same assignee of this application in provisional application 62/054,009 incorporated herein by reference in its entirety, or any other computer-controlled or computer-assisted surgical device.

Reference will be made herein to the replacement of hip joints and knee joints and it should be understood that the present invention may be applied to other joints within the body and any other bones found within the body. These other joints that are repaired through resort to the present invention illustratively include the hip joint, shoulder joint, ankle joint, wrist joint, finger joint, toe joint, or other joint. As used herein, a subject is defined as a human; or an animal of a non-human primate, a horse, a cow, a sheep, a goat, a dog, a cat, a rodent, and a bird.

Embodiments of the present invention provide a method that uses a known geometry of a patient's implant to provide fast and accurate intraoperative registration to the patient's pre-operative plan during revision arthroplasty. Embodiments of the inventive concept include segmentation of the geometry of the patient's implant, scanned via computed tomography (CT), followed by registration of the implant manufacturer's three-dimensional (3D) model; thus an accurate and predictable digitizing target is available. Alternatively, bi-planar X-rays rather than CT may be used to register to the implant manufacturer's 3D model onto the patient. The pre-operative plan may be created on the bi-planar X-rays that is then transformed to a 3-D implant plan which is positioned relative to the manufacturing model. Remaining bone stock after implant removal is measured so that the best plan may be selected from a set of preoperative plans. Embodiments of the inventive method are advantageous because the geometry of an implant is known to a much higher precision than a patient's operative bone. The methods for segmenting the implant in the digital imaging and communication in medicine (DICOM) standard files are advantageous because it requires less computational steps and time when compared to bone segmentation. Additionally, the use of a manufacturer's 3D model of the patient's implant requires far fewer digitizing points for intraoperative registration as compared with the conventional method of digitizing to bone. An accurate implant model allows for accurate digitizing to a patient's entire operative bone without requiring the digitizing of any part of the anatomy outside the surgical field. Accuracy of scanning and/or segmenting bone only affects planning accuracy rather than both planning accuracy and digitizing accuracy. If implants are planned to DICOM standard files and not solid models of the bones, then segmentation of bones is unnecessary.

In a specific embodiment of the inventive method, given only an implant model library and a system for making navigated cuts along one or more surfaces of an implant, where the surfaces are planar or other arbitrary geometries that are cemented or non-cemented, coordinates of surface points are collected from the exposed surface of the implant, for example a tibia tray during revision total knee replacement (TKR) surgery. Subsequently, the system finds the best-fit match between the collected surface coordinates and the 3D implant models in the implant library. After the best-fit implant is determined, the 3D implant model is registered to the patient's digitized implant and thus the patient's operative bone. The user may then remove the implants using conventional methods. The remaining bone stock after implant removal is measured so that the best plan may be selected from a set of preoperative plans and the bone is prepared for the new implants using navigated systems, a robotic system, or an articulating hand-held system such as those described above.

In one embodiment of the inventive method, given only an implant model library and a system for making navigated cuts along one or more surfaces of an implant, where the surfaces are planar or other arbitrary geometries that are cemented or non-cemented, coordinates of surface points are collected from the exposed surface of the implant, for example a tibia tray during revision total knee replacement (TKR) surgery. Subsequently, the system finds the best-fit match between the collected surface coordinates and the 3D implant models in the implant library. After the best-fit implant is determined, the 3D implant model is registered to the patient's digitized implant and thus the patient's operative bone. The cutting device under navigation, with a robotic system or an articulating drill system is then used to separate the joined surfaces until there is enough separation to remove the implant without causing further significant damage to the bone.

For example, in a revision TKR surgery, the drill tip of a navigated, self-articulating handheld cutting tool as disclosed in provisional application 62/054,009 is used to trace the surface of the implant (after removal of the liner) while collecting 3D coordinates in the navigation space. The collected coordinates are then best-fit to a library of tibial trays, and a plane is computed in space from the now registered tray geometry where the bottom of the tray is located. Subsequently, the cutter is positioned in the approximate position where the plane would be such that the cutter removes material below the tibial tray, and the cutter is allowed to self-articulate and lock into a tracking mode relative to the plane. The cutter is turned on, and proceeds to carefully cut the plane that the cutter orientation is locked to, even in the presence of bone motion. The operator carefully cuts around the keel by reviewing feedback information, possibly of a graphical nature, that identifies the current position of the drill relative to the keel. Once the cutting around the keel is complete to the degree the surgeon feels is adequate, the tibial tray is pulled off, leaving a planar bone surface. If there is cement left on the tibia surface, the operator may indicate to the system that the plane should be cut to a lower depth, and then repeat the cutting to shave off the rest of the cement. In this way, the present invention reduces the manual removal of bone cement. In one embodiment, the hand-held articulating system may include a degree of freedom that ensures the keel is not cut. For example, the NavioPFS system (Blue Belt Technologies) has a hand held device whereby the cutter actuates linearly. The system can actively avoid impacting the keel of the tibial baseplate due to the active linear actuation as the user moves the cutter.

Alternatively, a user could locate the bottom of the tray or the cement layer without an implant model, for example using the tip of the cutter of a navigated, self-articulating handheld cutting tool. The user, after removing the tibial liner, may digitize points on the top of the tibial tray to define that plane in navigated space. The user then collects a point at the cement layer or bottom of the tray that would designate the offset distance between the tibial tray plane and the cement layer or bottom of the tray. The user then holds the articulating cutter parallel to the top plane but offset down to the cement layer or bottom of the tray to remove the implant or cut through the cement. In this way, the present invention reduces the manual removal of bone cement, and preserves healthy bone without the need of the manufacturers implant model.

Furthermore, when either or both the femoral and tibial components are loose, the cement typically has a detached, uneven surface; however, the cement does have flat surfaces on the tops of the pieces of the femoral and tibial components that are still attached to the bone. The position of the implant on the bone may be determined by simply digitizing the tops of the flat surfaces of the cement and either creating a generic set of five-planes or registering the known geometry of the internal surfaces of the implant, which could then be used to execute 1) a pre-surgical plan, 2) a bone resurfacing to clean off the cement, or 3) a shift in implant position, e.g. a few millimeters proximally for a femur, which may then be executed with the hand-held device.

It should be appreciated that the methods for implant removal may similarly be used with a navigated device and/or a robotic assistance device. For example, the 3D coordinates of the tibial tray, the flat surfaces of the bone cement, the bottom of the tray and/or the cement layer may be defined and/or collected using an optical or mechanical digitizer probe in communication with an optical tracking system, navigation system, robotic system, and any combination thereof. The coordinates could be used to aid in implant removal, for example, cutting between the implant and the bone. Or the data could be used to define generic set of five-planes or registering the known geometry of the internal surfaces of the implant, which could then be used to execute 1) a pre-surgical plan, 2) a bone resurfacing to clean off the cement, or 3) a shift in implant position, e.g., a few millimeters proximally for a femur, which may all be executed with a navigated system or a robotic system such as those described above.

In another embodiment, a clamp on a robotic system may be attached to the existing implant at a specified location. The position of the clamp on the implant provides the robotic system with the position and orientation of the implant, therefore no digitization is required. The robotic system then executes the pre-operative plan relative to the implant, for example, by cutting under or around the implant to remove it while executing the pre-operative plan for the new implants simultaneously.

The embodiments disclosed herein may also be used in revision unicompartmental knee surgery. The implant is similarly scanned, segmented and used for registration. After the UKA implant has been registered intraoperatively, the existing implant can be removed by conventional methods, with navigated systems, robotic systems, or hand-held articulating systems. Navigation systems, robotic systems, or a hand-held articulating system may then be used to prepare the bone where the existing implant is, on the opposite side of where the implant is, or the whole bone can be prepared for a total knee revision case depending on the diagnosis and needs of the patient. For example, if a patient has a lateral unicompartmental knee replacement, the lateral implant may be used for registration for a surgical procedure. The surgical procedure could be a revision case on the lateral side of the knee, or could be a primary unicompartmental knee replacement of the medial side of knee, or could be for a total knee replacement procedure. The implant provides a registration tool for all of the anatomy in an operative area.

In cases of revision total hip arthroplasty where the existing prosthesis is well fixed in the bone and difficult to remove, significant bone may have to be removed to the distal portion of the prosthesis. In one embodiment the user can digitize the exposed prosthesis in the proximal portion of the femur registering the prosthesis to the manufacturer's model and thereby registering to a pre-operative plan. Once registered, the system allows a clean osteotomy at the distal end of the prosthesis as planned by the surgeon. Since the surgeon cannot visually see the implant within the bone, the system eliminates any guess work or the drilling of multiple holes in the bone to determine prosthesis location. Subsequently, the system may prepare the exposed bone stock for insertion for a secondary prosthesis. The system may be any of a navigated system, robotic system, or hand-held articulating system.

Additionally, in revision total hip joint replacement, cement removal is often desired to properly prepare the canal for the new implant. In one embodiment, after registering an implanted prosthesis to the manufacturer's model, the system may be used to provide navigated ultrasonic cement removal around the prosthesis to facilitate prosthesis removal. The system may activate an ultrasonic tool when it is located within a specific distance of the implant surface. This will keep the tool operating in a defined "safe zone" and reduces the risk of any harm caused to surrounding tissue. For example, a navigated system, robotic system, or hand-held system may be used to localize an ultrasonic device such as the OSCAR 3 (Orthosonics) so that it is at a safe distance to remove bone cement that may have been identified in pre-operative images.

In another embodiment, implant specific guides may be created which seat perfectly on the implant. The guides have positions for the saw slots such that the new knee implant is positioned precisely relative to the pre-operative plan. Alternatively, implant specific pin guides may be used. The guide seats on the implant perfectly and shows the surgeon where to place the pins which are part of the pre-operative plan. Next, the implant is removed, and cutting guides are then fixed to the guide-placed pins which are then used to finish the plan.

A system and method for performing robotically assisted surgery is described in U.S. Pat. No. 5,086,401. Computer-assisted imaging and probe tracking systems are described in U.S. Pat. Nos. 5,383,454; 5,198,877; and WO 91/07726. Referring now to FIG. 1, an exemplary system is shown generally at 10 capable of implementing the revision methods of the present invention for robotic assisted surgery. The system 10 includes both a presurgical planning workstation 12 and a library of implant designs 14, for example, in the form of CAD model data sets 15. A bone image data set 16, for example representative of a CT bone image, is obtained and transferred into the presurgical planning workstation 12. The user, such as a treating physician or an assistant working with the treating physician, is able to work at the presurgical planning workstation to select and position a suitable implant design within the patient's bone. Details of such presurgical planning are well described in the literature relating to the ORTHODOC presurgical planning system cited above.

The system 10 also includes a robotic surgical system 20 that includes a robotic controller 22 such as a digital processor in the form of a programmable computer, an online display screen 24, and a robot arm 26. The robot arm 26 can be any conventional industrial robot having a manipulatable robotic arm 28 that has at least 5 axes and capable of high precision placement. In some embodiments, a force-torque sensor 30 is mounted at the distal end of arm 28, and an end-effector in the form of a probe 32 or a surgical cutting tool (not shown) may be attached to the force-torque sensor.

The robotic system 20 further includes a safety processor 44, and a real time monitoring computer 46. The force-torque sensor 30, the safety processor 44, the real time monitor 46, and a bone motion monitor 50, each help monitor the position, slippage, and blockage of the effector end of the manipulatable arm 28. In some embodiments, the bone 60 (e.g., a femur) is held in place in a fixator assembly 52. Real time monitoring of these parameters may help assure that the robotic system is operating as planned. Details of these monitoring systems are described in the literature cited above which describes the ROBODOC robotic surgical system (THINK Surgical, Inc., Fremont, Calif., USA).

In some inventive embodiments, a digitized bone data set including the coordinate positions of a number of surface locations on the bone as measured by a bone digitizer arm registered to the robotic coordinate system. Accordingly, system 10 further includes bone digitizer arm 100, for example, as described in commonly owned U.S. Pat. No. 6,033,415. An acquired digitized bone data set 17, is obtained by a digitizer arm 100 and is used to transform bone image data set 16 into the robotic coordinate system. It is appreciated that a data set such as DICOM is readily obtained from additional source.

Examples

Example 1: Revision TKR Procedure (Restore Current Implant's Joint Line)

In an implementation of an embodiment of the inventive method for a revision TKR procedure to restore the joint line of the patient's current implant, the procedure is carried out in a three-step protocol which includes a pre-operative protocol, intraoperative protocol: registration, and intraoperative protocol: surgical procedure.

An embodiment of the pre-operative protocol of the inventive embodiment for the revision TKR includes the steps of: acquiring a CT scan of the operative bones with the installed implants; segmenting the installed implant from the volumetric data; segmenting the bone outside the implant region (this is for pre-operative planning only and is not required intraoperatively); determining the implant make/model/size, and registering the manufacturer's 3D model to the segmented implant in the patient, thus providing a transformation matrix between manufacturer's 3D model and the patient's DICOM data. The implant may be determined automatically by determining which implant make, model, and size best matches the segmented implant, or the implant can also be manually specified if the make, model, and size are known. Surgery is planned relative to DICOM data using any procedure. For a given implant, there are several pre-packaged plans that depend on the amount of bone that is remaining after implant removal. The surgical plans place the articular surfaces of the new implants aligned with the articular surfaces of the installed (old) implant. The surgical plans differ in the amount that the new planar cuts are offset from the old planar cuts. In certain inventive embodiments, the plans are automatically generated relative to the old implant (manufacturer's model), and all the plans are available in the operating room where the procedure is to be performed.

An inventive embodiment of the intraoperative protocol includes registration of the inventive embodiment for the revision TKR by: digitizing the patient's implant which is rigidly fixed to the patient's operative bone; registering the digitized implant to the nominal 3-D model, thus providing the transformation matrix between the digitized implant and the manufacturer's 3-D model; and computing the transformation matrix between the digitized implant and the patient's DICOM data, thereby registering the entire patient's operative bone to the set of pre-operative plans.

An embodiment of the intraoperative protocol: surgical procedure of the inventive embodiment for the TKA restoration includes the steps of: proceeding to remove prosthetic components from the patient, and after removing the component, measuring the amount of bone removed during extraction in various planes illustratively including Anterior-Posterior, Proximal-Distal, and other directions; choosing the plan which places the new planar cuts within the remaining bone stock; cutting the bones using the robot and drilling the intramedullary canals; implanting the femoral component, using appropriate shims to compensate for added bone removal such that the previous implant articular surface is restored; and implanting the tibial component, using appropriate poly thickness to compensate for added bone removal such that the previous implant articular surface is restored. As used herein, poly refers to polymer contact surfaces conventional to TKA implants that illustratively include polyethylene of varying degrees of cross-linking; other polyalkylenes, fluorinated polyalkylenes, and copolymers thereof.

Example 2: Revision TKR Procedure (New Joint Line Perpendicular to Mechanical Axis)

In an implementation of an embodiment of the inventive method for a revision TKR to make a new joint line perpendicular to the mechanical axis, the procedure may be carried out in a three-step protocol that includes a pre-operative protocol, intraoperative protocol: registration, and intraoperative protocol: surgical procedure.

An embodiment of the pre-operative protocol of the inventive embodiment for the revision TKR includes: acquiring a CT scan of the bone with the installed implant; segmenting the installed implant; segmenting the bone outside the implant region: pre-operative planning only, and not required intraoperatively; determining the implant make/model/size, and registering the manufacturer's 3D model to the segmented implant in the patient, thus providing a transformation matrix between manufacturer's 3D model and the patient's DICOM data. The implant may be determined automatically by determining which implant make, model, and size best matches the segmented implant, or the implant may also be manually specified if the make, model, and size are known. Anatomic landmarks are located on the DICOM data that are available in the operating room where the procedure is to be performed.

An embodiment of the intraoperative protocol: registration of the inventive embodiment for the TKA restoration includes the steps of: digitizing the patient's implant which is rigidly fixed to the patient's operative bone; registering the digitized implant to the nominal 3D model, thus providing the transformation matrix between the digitized implant and the manufacturer's 3D model; and computing the transformation matrix between the digitized implant and the patient's DICOM data, thereby registering the entire patient's operative bone to the set of anatomic landmarks.

Figure 2A:
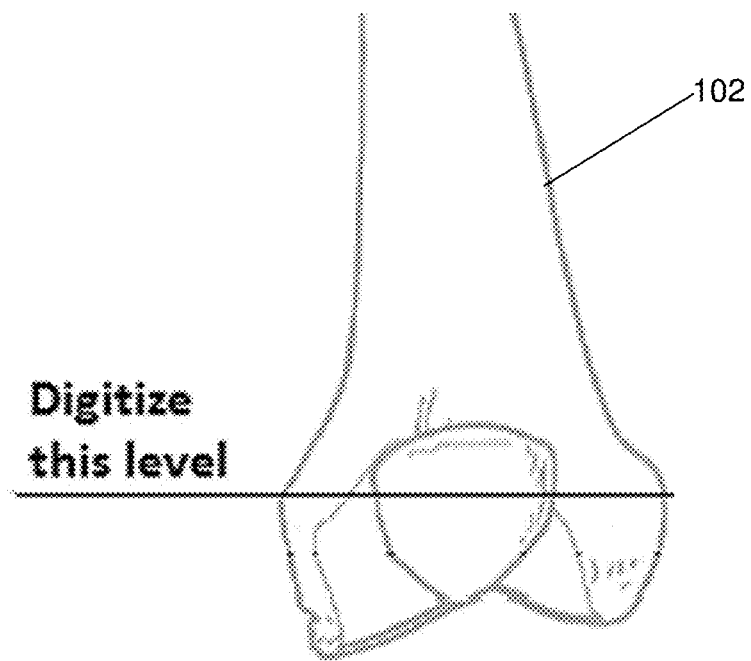
FIGS. 2A-2C depict a femur bone and the making of a distal planar cut orthogonal to the mechanical axis, and chamfering for an implant, respectively in accordance with an embodiment of the invention.
Figure 2B:
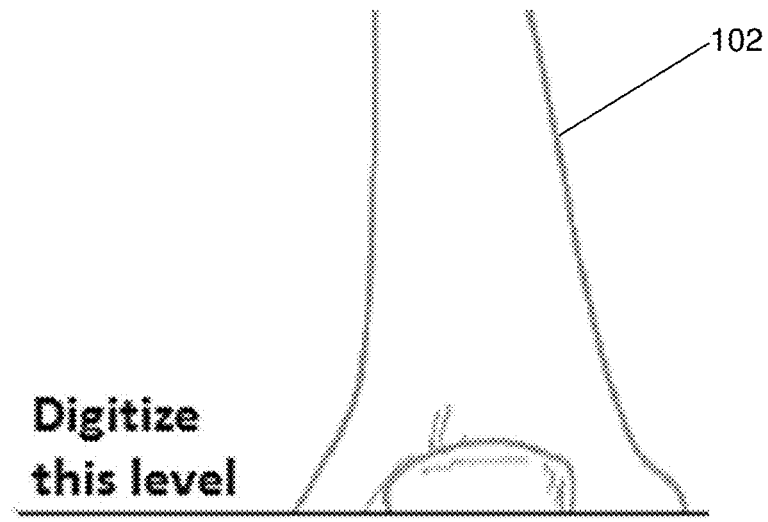
Figure 2C:
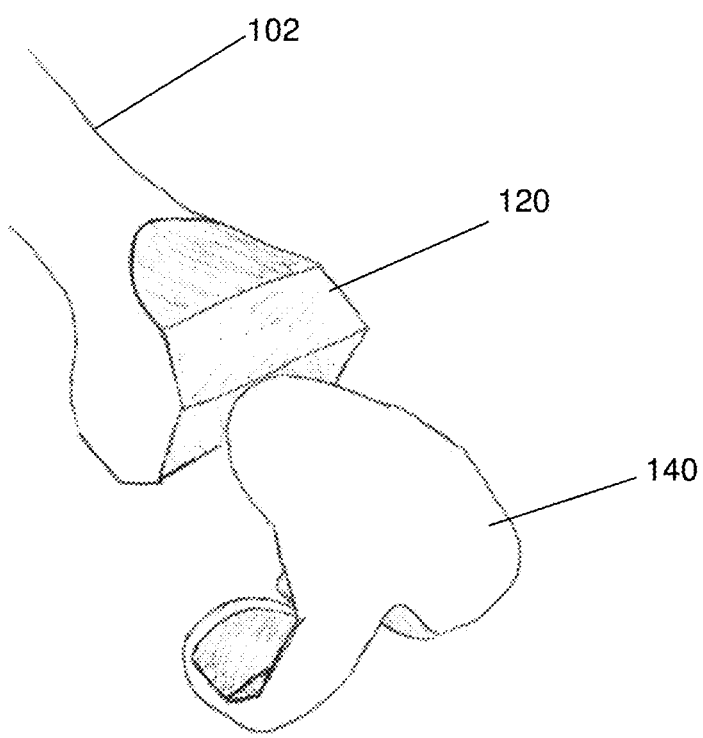

An embodiment of the intraoperative protocol: surgical procedure of the inventive embodiment for the TKA restoration includes the steps of: proceeding to remove prosthetic components from the patient; digitizing the proximal-distal level of the femur using a single point to make a distal planar cut orthogonal to the mechanical axis, and then making chamfer cuts specific to the new implant model and size the surgeon wishes to use (as shown in FIGS. 2A, 2B, and 2C, respectively for femur 102, chamfer cuts 120, and implant 140); and digitizing the proximal-distal level of the tibia using a single point to make a distal planar cut orthogonal to the mechanical axis (similar to femoral preparation), and then tibial shaping is performed specific to the implant model and size the surgeon wishes to use. In a variation to the above steps in a specific embodiment no pre-operative planning or anatomical landmarks are performed or made, and cut positions are generated intraoperatively.

Example 3: Revision THR Procedure

In an implementation of an embodiment of the inventive method for revision THR to restore a hip implant, the procedure may be carried out in protocol steps that include a pre-operative protocol, and an intraoperative protocol: with registration and surgical procedures.

An embodiment of the pre-operative protocol of the inventive embodiment for the revision THR includes the steps of: acquiring a CT scan of the bone with the installed implant; segmenting the installed implant; segmenting the bone outside the implant region: for pre-operative planning only, and not required intraoperatively; determining the implant make/model/size, and registering the manufacturer's 3D model to the segmented implant in the patient, thus providing a transformation matrix between manufacturer's 3D model and the patient's DICOM data. The implant may be determined automatically by determining which implant make, model, and size best matches the segmented implant, or the implant may also be manually specified if the make, model, and size are known. Surgery is planned relative to DICOM data using any procedure. For a given implant, there are several pre-packaged plans which depend on the amount of bone that is remaining after both implant and cement removal. During the surgical planning, the goal is to achieve the desired leg length, offset, anteversion angle, and range of motion, while ensuring that the new implant component position is well-seated in bone. Multiple plans may be created which depend on the amount of remaining bone, with all the plans being available in the operating room where the procedure is to be performed.

Figure 3:
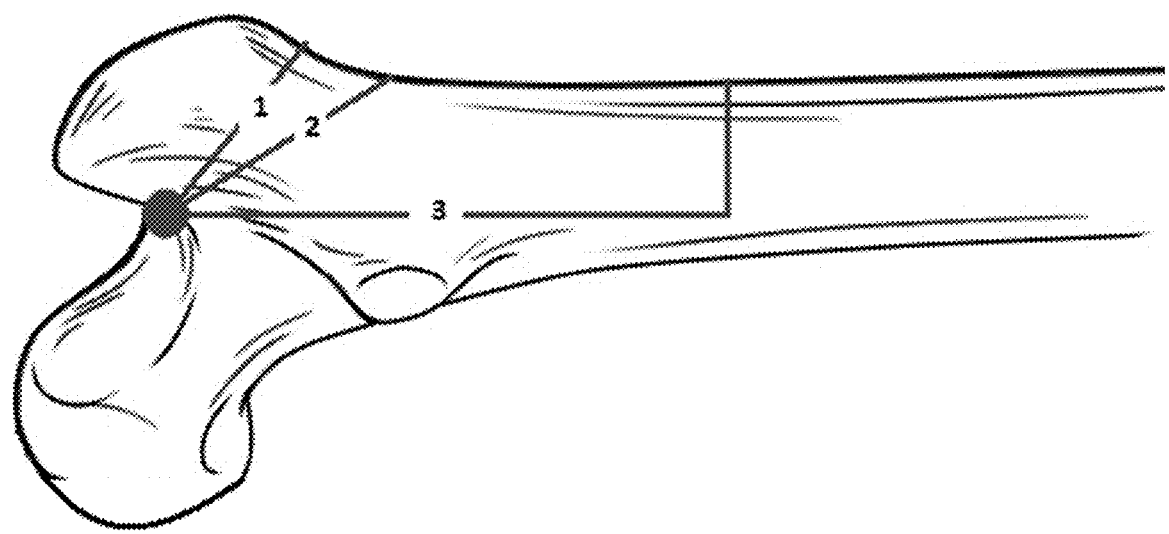
FIG. 3 depicts trochanteric osteotomies for hip stem implant removal in accordance with embodiments of the invention.

An embodiment of the intraoperative protocol of the inventive embodiment for the revision THR restoration includes:

A) Selecting whether a standard trochanteric osteotomy (1), a trochanteric slide osteotomy (2), or an extended trochanteric osteotomy (3) will be performed as represented in FIG. 3.

B) Registration
  i. Digitize the most superiorly exposed intersection of the implant and bone (approximately where the dot is in FIG. 3)
  ii. If necessary, drill several holes within the osteotomy region to digitize additional points along the implant for improved registration
  iii. Digitize the "terminal," or distal, endpoint of the trochanteric osteotomy along the lateral shaft of the femur OR digitize the osteotomy path on the surface of the bone.
  iv. Register the digitized implant to the nominal 3-D model, thus providing the transformation matrix between the digitized implant and the manufacturer's 3-D model.
  v. Compute the transformation matrix between the digitized implant and the patient's DICOM data, thus registering the entire patient's operative bone to the set of pre-operative plans C) Remove the implant D) Measure the remaining bone stock and select the appropriate plan E) The robotic surgical system cuts the patient's femur per the pre-operative plan using the 3-D model of the new implant F) Perform any additional bone preparation manually G) Insert desired implant As a person skilled in the art will recognize from the previous detailed description and from the figures and claims, modifications and changes can be made to the preferred embodiments of the invention without departing from the scope of this invention defined in the following claims.

The invention claimed is:

1. A method for registering a pre-operative plan to a bone with an installed implant thereon, the method comprising:
  obtaining image data of the bone and the installed implant thereon;
  segmenting the installed implant from the image data to yield segmented implant data;
  obtaining a nominal 3-D model of the installed implant;
  registering the nominal 3-D model of the implant to the segmented implant data providing a first transformation matrix between the nominal 3-D model and the image data;
  generating a pre-operative plan relative to the image data;
  digitizing the installed implant on the bone;
  registering the digitized implant to the nominal 3-D model providing a second transformation matrix between the digitized implant and the nominal 3-D model; and
  registering the pre-operative plan to the bone by computing a third transformation matrix using the first transformation matrix and the second transformation matrix.

2. The method of claim 1 further comprising segmenting the bone from the image data, wherein the generation of the pre-operative plan is relative to at least one of the image data or the segmented bone.

3. The method of claim 2 wherein generating the pre-operative plan comprises planning the placement of a new implant relative to remaining bone outside the segmented implant.

4. The method of claim 3 wherein a plurality of pre-operative plans are generated to account for an unknown amount of bone remaining after the installed implant is removed from the bone.

5. The method of claim 1 wherein the nominal 3-D model of the implant is obtained by automatically determining a preformed implant make, model, and size match to the segmented implant.

6. The method of claim 1 wherein the nominal 3-D model of the implant is obtained by specifying a known make, model, and size of the installed implant.

7. The method of claim 1 wherein the implant is a knee implant or a hip implant.

8. A method for registering a pre-operative plan to a bone with an installed implant thereon, the method comprising:
   obtaining image data of the bone and the installed implant thereon;
   segmenting the installed implant from the image data to yield segmented implant data;
   generating a pre-operative plan relative to the segmented implant data;
   obtaining a nominal 3-D model of the installed implant;
   registering the nominal 3-D model of the implant to the segmented implant providing a first transformation matrix between the nominal 3-D model and the segmented implant;
   digitizing the installed implant on the bone;
   registering the digitized implant to the nominal 3-D model providing a second transformation matrix between the digitized implant and the nominal 3-D model; and
   registering the pre-operative plan to the installed implant by computing a third transformation matrix using the first transformation matrix and the second transformation matrix.

9. The method of claim 8 wherein generating the pre-operative plan comprises planning the placement of a new implant relative to one or more planes associated with the segmented implant.

10. The method of claim 9 wherein a plurality of pre-operative plans are generated to account for an unknown amount of bone remaining after the installed implant is removed from the bone.

11. The method of claim 8 wherein the nominal 3-D model of the implant is obtained by automatically determining a preformed implant make, model, and size match to the segmented implant.

12. The method of claim 8 wherein the nominal 3-D model of the implant is obtained by specifying a known make, model, and size of the installed implant.

13. The method of claim 8 wherein the implant is a knee implant or a hip implant.

14. A method for registering a pre-operative plan to a bone with an installed implant thereon, the method comprising:
   obtaining image data of the bone and the installed implant thereon;
   segmenting the installed implant from the image data to yield segmented implant data;
   obtaining a nominal 3-D model of the installed implant data;
   registering the nominal 3-D model of the implant to the segmented implant providing a transformation matrix between the nominal 3-D model and the segmented implant;
   generating a pre-operative plan relative to the nominal 3-D model registered to the segmented implant;
   digitizing the installed implant on the bone; and
   registering the digitized implant to the nominal 3-D model providing a transformation matrix between the installed implant and the pre-operative plan.

* * * * *